US008003135B2

(12) United States Patent
Back et al.

(10) Patent No.: US 8,003,135 B2
(45) Date of Patent: Aug. 23, 2011

(54) NATURAL EXTRACT CONTAINING XANTHOHUMOL, AND METHOD FOR THE PRODUCTION THEREOF PRODUCTS PRODUCED THEREFROM

(75) Inventors: Werner Back, Freising (DE); Achim Zürcher, Rheinfelden (CH); Sascha Wunderlich, Freising (DE)

(73) Assignee: TA-XAN AG, Wiesbaden (DE)

( * ) Notice: Subject to any disclaimer, the term of this patent is extended or adjusted under 35 U.S.C. 154(b) by 0 days.

(21) Appl. No.: 11/793,889

(22) PCT Filed: Dec. 22, 2005

(86) PCT No.: PCT/EP2005/013916

§ 371 (c)(1), (2), (4) Date: Jun. 21, 2007

(87) PCT Pub. No.: WO2006/066941

PCT Pub. Date: Jun. 29, 2006

(65) Prior Publication Data

US 2008/0008776 A1 Jan. 10, 2008

(30) Foreign Application Priority Data

Dec. 22, 2004 (DE) ........................ 10 2004 063 125

(51) Int. Cl.
*A01N 65/00* (2009.01)

(52) U.S. Cl. ...................................................... 424/725

(58) Field of Classification Search ........................ None
See application file for complete search history.

(56) References Cited

U.S. PATENT DOCUMENTS

2005/0019438 A1 1/2005 Bourges-Sevenier et al.

FOREIGN PATENT DOCUMENTS

| | | | |
|---|---|---|---|
| DE | 19939350 | * | 2/2001 |
| DE | 10256166 | * | 6/2004 |
| DE | 10320250 | | 12/2004 |
| EP | 0679393 | | 11/1995 |
| EP | 1415657 | | 5/2004 |
| WO | WO 03090555 | | 11/2003 |

OTHER PUBLICATIONS

The ingredients in beer, 3 pages, 2009.*
Walker, Caroline J., et al., "Untersuchung zum hohen Xanthohumol-Gehalt in Bieren vom Typ Stout/Porter", *Brauwelt*, (2003),1709-1712.

* cited by examiner

*Primary Examiner* — Michael Meller
(74) *Attorney, Agent, or Firm* — Greenblum & Bernstein, P.L.C.

(57) ABSTRACT

The invention relates to a method for producing an extract containing xanthohumol (XN), which is obtained from toasted cereal products, cereal malt, coffee or cocoa. The XN-content in said extract is in the region of 10 mg/kg-2 g/kg xanthohumol. The use of XN-toasted extracts enables the XN-content of foodstuffs and pharmaceutical products to be increased in a natural manner.

36 Claims, No Drawings

NATURAL EXTRACT CONTAINING XANTHOHUMOL, AND METHOD FOR THE PRODUCTION THEREOF PRODUCTS PRODUCED THEREFROM

CROSS REFERENCE TO RELATED APPLICATIONS

This application is a 35 U.S.C. §371 U.S. National Phase of International Application No. PCT/EP2005/013916, filed Dec. 22, 2005, the contents of which are incorporated herein by reference.

TECHNICAL FIELD

The present invention relates to a method for producing a roasted extract from cereals, cereal malt or coffee comprising xanthohumol (XN) and a hop extract comprising xanthohumol as well as its use for the production of beverages and/or food products.

BACKGROUND ART

Hop is used as raw material for the production of beer. Hop provides the bitter impression of beer but also an elongated shelf life due to its antibacterial effect.

The most important compounds contained in hop are, besides the bitter acids (e.g. α-acids), essential oils, tannins and polyphenols.

Xanthohumol, a prenylflavonoid (polyphenol) of hop which occurs in the lupulin glands of the hop cones has a plurality of positive effects. Beside the antiviral and the anti-oestrogenic and anti-inflammatory effect, a cancer-chemo preventive activity of XN is also discussed which activity is currently under investigation in animal experiments. The content of xanthohumol in hops varies depending on the hop variety between 0.1 and 1%. The hop varieties having a high content of xanthohumol usually comprise a high portion of bitter substances.

Hop products may be divided in raw hops, hop pellets and hop extracts. Since xanthohumol occurs only in the lupulin glands of the hop cone, hop pellets exhibit a high content of XN corresponding to the accumulation of α-acids. Hop extracts may be obtained by extraction with $CO_2$ and/or ethanol. Whereas $CO_2$ extract hardly comprises any xanthohumol XN is extracted almost completely during the ethanol extraction. Recently, XN enriched products are produced by a combination of both extraction methods. Depending on the production method XN contents of between 8 and 99% are achieved. The production of hop extracts enriched with XN and drinks comprising XN is described e.g. in the patents DE 19939350, DE 10256031, DE 10240065 and EP 1431385.

In the brewing process xanthohumol is relatively instable and is mainly precipitated via the trub, the yeast, by filtration and stabilisation due to its limited solubility. Besides, xanthohumol is isomerised to iso-xanthohumol which also has a positive effect, however, to quite a lower extent compared to xanthohumol. With the conventional method less then 0.2 mg/l XN are reached in the final beer in most of the cases. In some stout or porter type dark beers XN contents of up to 1.2 mg/l XN were found (Walker et al., Brauwelt 2003). With a special brewing method which applies late hopping and a fast cooling of the beer wort it is possible to increase the XN content in non-filtered pale beers to 1-10 mg/l (DE 102 56 166).

It is an advantage of the present invention that the isomerisation of xanthohumol to iso-xanthohumol is suppressed to a large extent due to the improvement of the brewing method. Therefore, it is possible to increase dosage amounts of XN without allowing the beers to become unpleasantly bitter, for instance. Further, the addition of stabilisers is possible which would normally lead to a relevant decrease in the XN content.

A method for producing the roasted extract comprising XN from roasted products of cereals, cereal malt, coffee or cacao and a hop extract comprising XN is an object of the present invention. The hop extract comprising XN is characterised by a particularly high content of xanthohumol. It is in the range from 10 mg to 2 g/kg, preferably in the range of 200 mg to 850 mg/kg. Due to the use of this roasted extract beers with a significant increased content of XN compared to the prior art can be obtained in accordance with the German purity law, for instance.

Herein, "roasted extract comprising XN" denotes an extract which is obtainable from a roasted extract from roasted products of cereals, cereal malt, coffee or cacao and from the hop extract comprising XN. "Roasted extract" denotes a cold or hot extract from coarsely ground or non-ground roasted malt or cereals and includes a hot or cold extract from coffee or cacao; "cereal malt" denotes a cereal that was artificially or controllably allowed to germinate, and "hop extract comprising XN" denotes an extract from hops which was obtained with the aid of a solvent and exhibits an increased content of XN. "Basic materials" is a collective term for plain or combined substances which may be of natural or synthetic origin. They are used as parent material for the further production of food products. In the present invention basic materials denote e.g. essences which may be enriched with XN as well as e.g. a basic material for coke according to an embodiment of the present invention.

For producing roasted extract comprising XN a hot aqueous extract of the ground roasted products e.g. of barley, wheat, rye as well as the corresponding malts, coffee beans or cacao beans is prepared. A hop extract comprising XN is added thereto at the beginning of the heating period. The extraction of xanthohumol in the extractions of the roasted products leads to a XN content which is by far higher than the solubility limit of XN in typical aqueous solutions. This amounts to 1.3 mg/l of XN at a water temperature of 23° C. and to 1.1 mg/l of XN at a water temperature of 8° C.

Soluble roasted substances which adsorb or bind XN and therefore, apparently keep it in solution, are probably responsible for the high yields of xanthohumol in the extracts. The extracts may be fermented, concentrated or clarified without noteworthy losses of XN. According to one embodiment of the present invention a xanthohumol content of approximately 1320 mg/kg was obtained in the extract after concentration of the XN comprising roasted malt wort.

The XN comprising roasted malt wort may be used in the food industry such as in the brewing and beverage industry as well as in the foodstuff industry. Thus, the application of the XN comprising roasted malt wort may lead to an enrichment of xanthohumol in spirits, herbal spirits, herbal liquor wine, beer, mixed drinks comprising beer, or bitters, and also of non-alcoholic drinks or drinks with reduced alcohol content such as malt beverages, coffee, coffee substitute, cacao, ice tea or soft drinks as well as of basic materials for the production of such products in a simple, safe and economic way. A particular advantage is that a roasted malt beer enriched with XN and prepared according to this method may be added to a conventionally produced beer at any time of the beer production in accordance with the purity law, i.e., without the use of emulsifying agents or other chemical additives.

An enrichment of food products with xanthohumol, such as bakery products, backing kits, parfaits, dairy products (e.g.

yoghurt, curd cheese and mixed drinks comprising milk) desserts, ice cream, meat products, sauces and herbal candies as well as enrichment of pharmaceutical products with xanthohumol, such as cough syrup, is also possible.

The method for preparing an aqueous extract comprising XN from roasted products of cereals, cereal malt, coffee or cacao comprises the following process steps:

a) addition of a hop product comprising XN to an extract which is mainly or completely produced from roasted or colour malts, respectively, or roasted barley; wherein the added hop product has a content of XN which is, related to the mass used for its production, at least 5 times that of the hops used for its production; and wherein after the addition of the hop product comprising xanthohumol to the aqueous roasted extract the dissolving or even an intensive dissolving of XN is reached, despite the original low solubility in aqueous solutions;

b) dissolving of XN by pre-dissolving of the XN comprising hop product in ethanol;

c) dissolving of XN by agitating, mixing, shaking, supersonic treatment, ultraturax treatment or other mechanical forces;

d) dissolving of XN by heating of the roasted extract;

e) dissolving of XN by application of an alternating current;

f) wherein the amount of the addition of the hop product comprising XN is at least 50 mg XN per liter.

As will be understood from the following examples, it is not necessary that all of the previously mentioned process steps are realised when implementing the process. The process steps b) to h) are optional.

In the following, examples of methods according to the present invention and beverages produced thereby are given.

EXAMPLE 1

Preparation of beer wort from a mixture of special malt comprising 1.9 kg of roasted barley malt (Carafa™, type 2, Fa. Weyermann, Bamberg) and 0.1 kg of Pilsen type malt. After mashing according to the congress method and mash separation 25 g/l of a hop extract enriched with XN were added (XanthoExtrakt, Simon H. Steiner Hopfen GmbH, XN 2.0%) during boiling of the roasted malt wort with the kettle-up wort concentration of 11% w/w (weight/weight percent) and a wort colour of 1650 EBC (European Brewing Convention). After separation of hot trub and a separation with diatomaceous earth the roasted malt wort comprising XN was concentrated in vacuo (200 mbar, ca. 55° C.) to an extract content of approximately 50% w/w. The syrup like extract ("density 1.25" kg/l) had a colour of approximately 7500 EBC and a content of xanthohumol of approximately 1320 mg/kg.

EXAMPLE 2

Preparing of beer wort from a special mixture comprising 0.05 kg of Pilsen type malt and 0.95 kg of roasted barley malt (Carafa™, Weyermann). After mashing according to the congress method and mash separation the wort was boiled for 2 hours. At the start of boiling 5000 mg/l of XN were added to the wort. For this, a hop extract comprising XN with 80% of diatomaceous earth and 20% of hop extract (XanthoExtrakt, Hopsteiner, XN 1.7%) was used. Beside XN, this extract also comprises α-acids and hard resins which have an influence on the flavour. The cast wort having a concentration of 11.7% w/w was fermented within 2 days by bottom fermenting brewer's yeast and was centrifuged after 5 days of storage.

The resulting roasted malt beer (RMB) had a colour of 1850 EBC and an XN content of 390 mg/l.

EXAMPLE 3

Method for preparing a roasted malt extract comprising XN according to example 1, however, the wort was fermented with brewer's yeast, centrifuged and filtered with diatomaceous earth prior to concentration. The roasted malt beer thus prepared and having an original extract of 12% and a colour of approximately 1700 EBC, had an XN content of 246 mg/l.

EXAMPLE 4

Method for preparing a roasted malt beer comprising XN according to example 3, however, the RMB was concentrated after the filtration in vacuo (200 mbar, ca. 55° C.) to an extract content of approximately 48%. The density of the syrup like roasted malt beer comprising XN was approximately 1.2 kg/l, the colour was 6900 EBC, and the XN content was 846 mg/kg.

EXAMPLE 5

Method for preparing a roasted malt extract comprising XN according to example 1, however, an amount of approximately 100 mg XN per liter of wort (11% w/w roasted malt extract) was dosed. Further treatment according to examples 3 and 4 gave a roasted malt beer with an extract content of 47% w/w, a density of 1.2 kg/l, a colour of 7200 EBC and a XN content of 341 mg/l.

EXAMPLE 6

Preparation of a coffee extract from 40 g of ground roasted coffee and 1 liter of hot water. After separation of the coffee grounds 100 mg of a hop extract comprising XN (XN content 80%) were added to the hot coffee extract. The hop extract was intensively mixed at temperatures of above 60° C. and it was further dissolved at 8° C. for 24 hours. After filtration of the coffee beverage comprising XN using a fluted filter the coffee beverage had an XN content of more than 12 mg/l.

EXAMPLE 7

Method for preparing a coffee beverage comprising XN according to example 6, however, the filtered coffee beverage was dried in a freeze drier to a water content of less than 10%. The soluble coffee beverage comprising XN had an XN content of 1042 mg/kg.

EXAMPLE 8

Approximately 1.8 g of the soluble coffee beverage comprising XN according to example 7 were mixed with 150 ml of hot water. The XN content of the mixed coffee beverage was approximately 10 mg/l.

EXAMPLE 9

To a non-filtered pale lager beer (XN content 0.1 mg/l) 2 g/l of the roasted malt beer comprising XN according to example 4 were added. Compared to the control beer a colour increase by 15 EBC and an enrichment of XN by 1.8 mg/l were detected in the bright beer.

EXAMPLE 10

To a non-filtered pale lager beer (XN content 0.1 mg/l) 20 g/l of the roasted malt beer comprising XN according to example 4 were added. The filtered beer had a colour of 120 EBC and a XN content of 13 mg/l.

EXAMPLE 11

To a filtered pale lager beer (XN content 0.05 mg/l) 20 g/l of the roasted malt beer comprising XN according to example 4 were added. The mixed filtered beer had a colour of 125 EBC and an XN content of 15 mg/l.

EXAMPLE 12

To a typical basic material for coke consisting of two components, coke essence, caramel colour and caffeine on the one hand, and phosphoric acid on the other hand, 880 g of a roasted malt beer comprising XN according to example 1 (concentration 1320 mg XN/kg) were added to 3.05 kg basic coke material and homogenised. After mixing of the enriched basic material with processed water (3:1000), carbon dioxide (6.2 g/l) and sugar (110 g/l) a xanthohumol content of 1.1 mg/l was determined in the ready-to-drink beverage.

EXAMPLE 13

To one kilogram of probiotic yogurt 2.29 g of roasted malt extract comprising XN according to example 1 is added and homogenised. In the pasteurised product a xanthohumol content of 0.3 mg/100 g was detectable.

EXAMPLE 14

To a pharmaceutical product, here 1 liter of cough syrup, a roasted malt extract comprising XN (7.6 g) according to example 1 was added. The resulting product comprised approximately 1.0 mg XN/100 ml.

The invention claimed is:

1. An aqueous liquid comprising xanthohumol (XN) and a roast extract, wherein the aqueous liquid comprises:

(i) a XN containing hop extract, and (ii) an aqueous extract of roasted products of at least one of cereals, malt, coffee, and cacao, the aqueous liquid comprising XN in a concentration of at least 50 mg/kg of liquid.

2. The aqueous liquid of claim 1, wherein the concentration of XN is up to 2 g/kg of liquid.

3. The aqueous liquid of claim 1, wherein the concentration of XN is from 200 to 850 mg/kg of liquid.

4. The aqueous liquid of claim 1, wherein (ii) comprises a cold or hot extract of at least one of coarsely ground or non-ground roasted malt, cereals, coffee and cacao.

5. The aqueous liquid of claim 4, wherein (ii) comprises an extract from roasted malt.

6. The aqueous liquid of claim 4, wherein (ii) comprises an extract from roasted cereals.

7. The aqueous liquid of claim 4, wherein (ii) comprises an extract from roasted coffee.

8. The aqueous liquid of claim 4, wherein (ii) comprises an extract from roasted cacao.

9. The aqueous liquid of claim 1, wherein (i) has been pre-dissolved in ethanol.

10. The aqueous liquid of claim 1, wherein (i) has been dissolved by at least one of agitating, mixing, shaking, supersonic treatment, and ultraturax treatment.

11. The aqueous liquid of claim 1, wherein (i) has been dissolved by heating.

12. The aqueous liquid of claim 1, wherein (i) has been dissolved by an alternating current.

13. The aqueous liquid of claim 1, wherein the liquid has a dry matter content of from 40 to 50% w/w.

14. The aqueous liquid of claim 1, wherein the liquid has a dry matter content of from 47 to 48% w/w.

15. The aqueous liquid of claim 1, wherein the liquid is present in at least partially fermented form.

16. The aqueous liquid of claim 15, wherein the aqueous liquid is present as a beer.

17. An aqueous liquid comprising xanthohumol (XN) and a roast extract, wherein the aqueous liquid comprises:

(i) a hop extract having a XN content of at least 0.5% w/w, and (ii) an aqueous extract of roasted malt, the aqueous liquid comprising XN in a concentration of at least 50 mg/kg of liquid.

18. The aqueous liquid of claim 17, wherein the liquid has a dry matter content of from 40 to 50% w/w.

19. The aqueous liquid of claim 17, wherein the concentration of XN is at least 200 mg/kg of liquid.

20. A beer to which the aqueous liquid of claim 17 has been added.

21. A method of producing the aqueous liquid of claim 1, wherein the method comprises combining a XN containing hop extract with a hot or cold aqueous extract of one or more of coarsely ground or non-ground roasted malt, cereals, coffee, and cacao.

22. The method of claim 21, wherein the hop extract has a XN content of at least 0.5 w/w.

23. The method of claim 21, wherein the aqueous extract is mainly or completely produced from roasted malt.

24. The method of claim 21, wherein the method further comprises concentrating the aqueous liquid.

25. The method of claim 24, wherein the aqueous liquid is concentrated to a dry matter content of from 40 to 50% w/w.

26. The method of claim 24, wherein the aqueous liquid is concentrated by at least one of heating, applying reduced pressure and freeze drying.

27. The method of claim 21, wherein the method further comprises at least partially fermenting the aqueous liquid with yeast.

28. The method of claim 21, wherein the hop extract is pre-dissolved in ethanol.

29. The method of claim 21, wherein the hop extract is dissolved by at least one of agitating, mixing, shaking, supersonic treatment, and ultraturax treatment.

30. The method of claim 21, wherein the hop extract is dissolved by at least one of heating and applying an alternating current.

31. The method of claim 21, wherein the aqueous extract is a hot extract.

32. The method of claim 21, wherein the aqueous extract is a cold extract.

33. A food product to which the aqueous liquid of claim 1 has been added.

34. The food product of claim 33, wherein the food product comprises an alcoholic beverage or a non-alcoholic beverage.

35. A pharmaceutical composition which comprises the aqueous liquid of claim 1.

36. The pharmaceutical composition of claim 35 which is a cough syrup.

* * * * *